US009464996B2

United States Patent
Marche et al.

(10) Patent No.: US 9,464,996 B2
(45) Date of Patent: Oct. 11, 2016

(54) PROCESSING DEVICE AND METHOD FOR THE SPECTROMETRIC MEASUREMENT OF A PHOTON FLUX

(75) Inventors: Eric Marche, ST Etienne de Crossey (FR); Caroline Boudou, Voreppe (FR); Patrick Radisson, Claix (FR)

(73) Assignee: Multix SA, Neuilly sur Seine (FR)

( * ) Notice: Subject to any disclaimer, the term of this patent is extended or adjusted under 35 U.S.C. 154(b) by 290 days.

(21) Appl. No.: 14/235,029

(22) PCT Filed: Jul. 23, 2012

(86) PCT No.: PCT/EP2012/064439
§ 371 (c)(1),
(2), (4) Date: Feb. 21, 2014

(87) PCT Pub. No.: WO2013/014132
PCT Pub. Date: Jan. 31, 2013

(65) Prior Publication Data
US 2014/0161226 A1    Jun. 12, 2014

(30) Foreign Application Priority Data
Jul. 26, 2011 (FR) ..................... 11 56832

(51) Int. Cl.
*G01N 23/06* (2006.01)
*G01T 1/17* (2006.01)

(52) U.S. Cl.
CPC ............. *G01N 23/06* (2013.01); *G01T 1/171* (2013.01)

(58) Field of Classification Search
CPC combination set(s) only.
See application file for complete search history.

(56) References Cited

U.S. PATENT DOCUMENTS

| | | | |
|---|---|---|---|
| 4,692,626 A | 9/1987 | Westphal | |
| 5,873,054 A | 2/1999 | Warburton et al. | |
| 7,408,160 B2 * | 8/2008 | Verbinski | G01N 23/02 250/358.1 |
| 7,504,636 B1 * | 3/2009 | Baxter | G01T 1/17 250/370.07 |
| 2004/0080659 A1 * | 4/2004 | Iwane | H04N 5/2254 348/342 |
| 2005/0174467 A1 * | 8/2005 | Kawai | H04N 5/228 348/335 |
| 2005/0242979 A1 * | 11/2005 | Hamilton | H04L 25/03834 341/144 |

FOREIGN PATENT DOCUMENTS

WO    03040757 A2    5/2003

* cited by examiner

*Primary Examiner* — Phillip A Johnston
*Assistant Examiner* — Hsien Tsai
(74) *Attorney, Agent, or Firm* — Baker & Hostetler LLP

(57) ABSTRACT

A processing device and method for a spectrometric measurement in terms of energy of a photon flux that may be received by a photosensitive element of a detector comprises the following successive steps: converting each photon received by the photosensitive element into an electrical signal, a characteristic of which is representative of the energy of the photon considered; filtering each electrical signal with a first low-pass filter whose cutoff frequency is adjusted as a function of the photon flux, the bigger the flux, the higher the cutoff frequency; determining the characteristic of each filtered electrical signal; generating an energy spectrum for the photon flux received as a function of the characteristic of the filtered electrical signals; and filtering the energy spectrum with a second low-pass filter whose cutoff frequency is adjusted as a function of the photon flux, the bigger the flux, the lower the cutoff frequency.

13 Claims, 2 Drawing Sheets

PROCESSING DEVICE AND METHOD FOR THE SPECTROMETRIC MEASUREMENT OF A PHOTON FLUX

CROSS-REFERENCE TO RELATED APPLICATIONS

This application is a National Stage of International patent application PCT/EP2012/064439, filed on Jul. 23, 2012, which claims priority to foreign French patent application No. FR 1156832, filed on Jul. 26, 2011, the disclosures of which are incorporated by reference in their entirety.

FIELD OF THE INVENTION

The invention lies in the field of imaging by ionizing radiation, notably by X-ray radiation. It applies to medical imaging and to non-destructive checking such as luggage checking. It relates to a device and a method for processing a photon flux.

BACKGROUND

X-ray radiation imaging systems are notably used for checking luggage in airports or in secure places. Such an imaging system comprises an X-ray radiation source subjecting the luggage to an X-ray photon flux and a semiconductor detector receiving the X-ray photons that have passed through the luggage. As a function of the absorption of the X-ray radiation by the luggage, it is possible to analyze the content of the luggage. The analysis of the content of the luggage and the evaluation of its dangerousness are steps which are more or less complex and automated depending on whether one is dealing with luggage intended for the hold or with passenger hand luggage carried into the cabin. In either case, the objective of X-ray radiation imaging systems is to detect dangerous substances such as explosives and inflammable matter. With the evolving of requirements in regard to security, it becomes necessary to be able to determine any type of substance so as, for example, to identify the presence of several substances which, combined together, can produce explosives. The detectors of contemporary X-ray radiation imaging systems generally comprise two superposed sensitive elements. A first sensitive element detects the photons of relatively high energy and a second sensitive element detects the photons of relatively low energy. These detectors, termed dual-energy, integrate the photons over the whole of the duration of exposure and lead to the measurement of two quantities of photons in two different energy ranges. They make it possible mainly to differentiate organic materials from inorganic materials. They also make it possible to determine the density of the materials traversed by the X-ray photons and therefore their composition. However, this density determination is not precise and leads to detection ambiguities. A reason for this lack of precision stems from the fact that the energy ranges of the two sensitive elements partially overlap. In practice, contemporary X-ray radiation imaging systems have difficulty in differentiating, among organic materials, certain commonly used materials from explosive materials.

More recently, X-ray radiation imaging systems have been developed so as to approximate a spectrometric measurement in terms of energy of a photon flux. These systems comprise several processing circuits each tailored to a given energy range. Certain systems comprise up to 8 processing circuits. However, these systems exhibit the drawback of being tailored only for a certain photon flux. Now, having regard to the diversity of the materials present in luggage, the photon flux may typically vary between $10^4$ and $10^8$ photons per square millimeter per second, i.e. a ratio of $10^4$. If the imaging system is tailored to a relatively small photon flux, a bigger photon flux leads to a degraded counting function, the photons no longer being counted individually. This results in a degraded image. Conversely, if the imaging system is tailored to a relatively big photon flux, the measurement of the energy of each photon is less precise, whatever the photon flux received.

SUMMARY OF THE INVENTION

An aim of the invention is notably to remedy all or some of the aforementioned drawbacks by allowing a spectrometric measurement in terms of energy of a photon flux which is tailored to this photon flux. For this purpose, the subject of the invention is a processing method for a spectrometric measurement in terms of energy of a photon flux that may be received by a photosensitive element of a detector. The method comprises the following successive steps:

converting each photon received by the photosensitive element into an electrical signal, a characteristic of which is representative of the energy of the photon considered, filtering each electrical signal with a first low-pass filter whose cutoff frequency is adjusted as a function of the photon flux, the bigger the flux, the higher the cutoff frequency, determining the characteristic of each filtered electrical signal, generating an energy spectrum for the photon flux received as a function of the characteristic of the filtered electrical signals, and filtering the energy spectrum with a second low-pass filter whose cutoff frequency is adjusted as a function of the photon flux, the bigger the flux, the lower the cutoff frequency.

The energy spectrum can be generated in the form of a histogram in which the classes are distinct energy ranges, the occurrence of each class being the number of photons whose energy lies in the energy range of the class considered. The generation of the spectrum in the form of a histogram makes it possible to adjust the cutoff frequency of the second low-pass filter by simply determining the number of classes of the histogram, the bigger the flux, the fewer classes the histogram comprises.

According to a particular embodiment, each photon received by the photosensitive element is converted into a pulse whose integral is proportional to the energy of the photon considered.

When the photon flux is received during predetermined and successive acquisition intervals, the cutoff frequencies of the first and of the second low-pass filter can be adjusted, for a given acquisition interval, as a function of the photon flux determined for the previous acquisition interval.

The photon flux is for example determined by the following steps:

determining the total photonic energy $E_T$ received by the photosensitive element during the previous acquisition interval, determining the mean photonic energy $E_M$ of the photons received by the photosensitive element during the previous acquisition interval, determining the ratio $N_{eff}$ of the total photonic energy $E_T$ to the mean photonic energy $E_M$, the quotient of said ratio $N_{eff}$ over a duration of the previous acquisition interval giving the photon flux.

The subject of the invention is also a processing device for a spectrometric measurement in terms of energy of a photon flux that may be received by a photosensitive element of a detector, the photosensitive element converting each photon into an electrical signal, a characteristic of which is representative of the energy of the photon received. The device comprises:

a shaping circuit comprising a first low-pass filter filtering each electrical signal, the cutoff frequency of the first low-pass filter being adjusted as a function of the photon flux, the bigger the flux, the higher the cutoff frequency, a measurement circuit determining the characteristic of each filtered electrical signal, a circuit for constructing spectra generating an energy spectrum for the photon flux received as a function of the characteristic of the filtered electrical signals, and a smoothing filter comprising a second low-pass filter filtering the energy spectrum, the cutoff frequency of the second low-pass filter being adjusted as a function of the photon flux, the bigger the flux, the lower the cutoff frequency.

The advantage of the invention is notably that it makes it possible to preserve substantially constant image quality whatever the photon flux received. Furthermore, the analysis of the composition of the objects by spectrometric measurement can also be substantially constant. Indeed, a poorly attenuating object, leading to a relatively big photon flux and to a relatively difficult energy spectral analysis, generally comprises only few materials to be identified. Conversely, a strongly attenuating object, leading to a relatively low photon flux and to a relatively easy spectral analysis, generally comprises several materials to be identified.

BRIEF DESCRIPTION OF THE DRAWINGS

The invention will be better understood and other advantages will become apparent on reading the description which follows, given in relation to appended drawings in which.

DETAILED DESCRIPTION

The invention applies to medical imaging and to the non-destructive checking of objects by ionizing radiation. It relates in particular to medium-energy X-ray radiation imaging systems, that is to say of energy lying between about 20 keV and 180 keV, and with large photon flux, that is to say whose flux lies between $10^4$ and $10^8$ photons per square millimeter per second.

Figure 1:
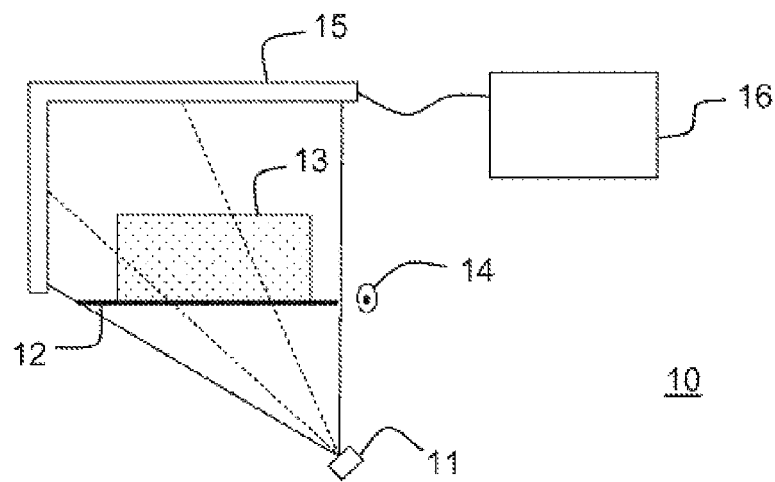
FIG. 1 schematically represents an X-ray radiation imaging system for luggage checking.

FIG. 1 schematically represents an X-ray radiation imaging system for luggage checking. The imaging system 10 comprises an X-ray source 11, a conveyor belt 12 able to transport luggage 13 in the direction represented by the arrow 14, a semi-conductor detector 15 and a processing device 16 connected to the detector 15. The detector 15 represented in FIG. 1 is an L-shaped linear detector. It comprises photosensitive elements such as photodiodes or photoconductors disposed on two mutually perpendicular lines. The detector 15 can also be a two-dimensional detector and comprise a matrix of photosensitive elements. When a photosensitive element of the detector 15 is exposed to an X-ray photon, it converts this X-ray photon into a packet of charges, the number of which is proportional to the energy of the photon. The X-ray source emits a photon flux toward the detector 15 across the conveyor belt 12. The spectrum of the X-ray flux received in the absence of objects is determined prior to the analysis of objects. Thus, by comparing this spectrum with the spectrum of the X-ray flux received in the presence of an object to be analyzed, it is possible to determine the X-ray flux absorbed by the object to be analyzed.

Figure 2:
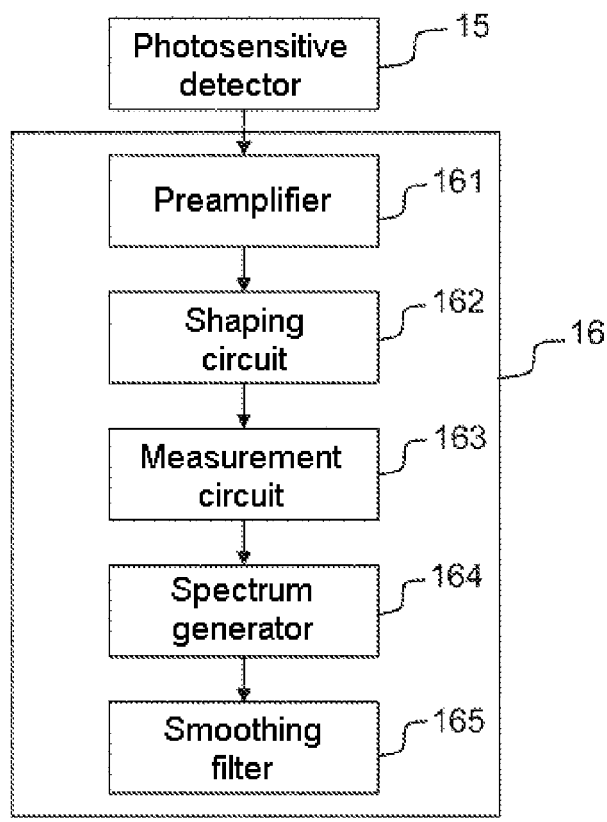
FIG. 2 represents, through a schematic, an exemplary processing device according to the invention.

FIG. 2 represents, through a schematic, an exemplary processing device according to the invention. The processing device 16 comprises a preamplifier 161 of integrator type, a shaping circuit 162, a measurement circuit 163, a spectrum generator 164 and a smoothing filter 165 forming a processing chain. The processing device 16 can either comprise a single processing chain for the whole set of photosensitive elements of the detector 15, in which case the packets of charges arising from the various photosensitive elements are processed successively, or comprise a processing chain for each photosensitive element, in which case the packets of charges are processed simultaneously. The preamplifier 161 is able to receive the packets of charge of a photosensitive element of the detector 15 and to transform each packet of charges into a voltage pulse whose integral is proportional to the number of charges of the packet of charges. The integral of each voltage pulse is therefore proportional to the energy of each X-ray photon received. The shaping circuit 162 filters each voltage pulse, as explained hereinbelow, and the measurement circuit 163 determines the characteristics of each filtered voltage pulse. In particular, the measurement circuit 163 can determine the maximum amplitude of each voltage pulse and its integral. An X-ray flux can be received either in a discontinuous manner for a given duration of acquisition, or in a manner which is continuous over time. In the latter case, the reception of the X-ray photons is sliced over time into successive acquisitions. The spectrum generator 164 constructs, for each acquisition and for each photosensitive element, an energy spectrum of the X-ray photons received over the duration of this acquisition by the photosensitive element considered. An energy spectrum can be represented in the form of a histogram in which the classes are distinct energy ranges, the occurrence of each class being the number of X-ray photons whose energy lies in the energy range of the class considered. In the processing device 16 described with reference to FIG. 2, the energy of the X-ray photons is converted into a voltage pulse whose integral depends on the energy of the X-ray photons. The energy spectrum can therefore be constructed by grouping the voltage pulses into various classes as a function of their integral. It is possible, during the generation of the energy spectra, to disregard voltage pulses whose properties (width, shape, etc.) do not seem coherent. A multiplicative factor can be applied so as to compensate for the disregarding of these voltage pulses. The smoothing filter 165 filters the energy spectrum, as explained hereinbelow. The invention is not only applicable to imaging systems in which the detectors convert the X-ray photons into packets of charges. It applies to any imaging system in which the detector-processing device assembly converts a photon into an electrical signal, at least one characteristic of which is representative of the energy of the photon received. The electrical signal can equally well be an analog signal or a digital signal. It is for example an impulse signal. The processing device then processes these signals so as to construct an energy spectrum on the basis of their characteristic.

In the processing device according to the invention, the shaping circuit 162 comprises a low-pass filter whose cutoff frequency is adjusted as a function of the X-ray photon flux. The bigger the X-ray photon flux, the higher the cutoff frequency. Stated otherwise, the more the X-ray photons arrive with a high mean frequency at the photosensitive elements of the detector 15, the more necessary it is to consider the voltage pulse over a short duration in order to avoid the pileups. One speaks of a pileup when two X-ray photons are received in too short a duration to be able to process each photon separately. For a relatively low X-ray photon flux, the measurement of the integral of a filtered pulse can be precise and not very noisy. The energy spectrum generated for the whole of the X-ray photon flux of a given acquisition may therefore be slightly noisy. One speaks of fine spectrometry. Conversely, for a relatively big X-ray photon flux, the measurement of the integral of a filtered pulse is relatively noisy. The energy spectrum generated for the whole of the X-ray photon flux of a given acquisition is therefore less precise. However, the higher cutoff frequency makes it possible to correctly ensure the X-ray photons counting function. The image obtained by counting the X-ray photons received by the various photosensitive elements of the detector 15 is therefore not degraded. The adjusting of the cutoff frequency of the low-pass filter as a function of the photon flux received therefore makes it possible to preserve substantially constant image quality whatever the photon flux received. As regards the spectrometric measurement, a strongly attenuating object leads to fine spectrometry, and a less attenuating object leads to degraded spectrometry. An analysis of the materials constituting an object based on the energy spectra generated for the various photosensitive elements is therefore less precise for a poorly attenuating object than for a strongly attenuating object. Nonetheless, a poorly attenuating object generally comprises only few superposed materials. Their identification is therefore facilitated thereby. Conversely, if the object is strongly attenuating, this is generally due to the fact that it comprises numerous superposed materials. The X-ray flux received is then not as big and leads to finer spectrometry. The various materials can therefore still be identified. The cutoff frequency of the low-pass filter of the shaping circuit 162 can be adjusted either individually for each photosensitive element of the detector 15 as a function of the X-ray photon flux received by this photosensitive element, or globally for all the photosensitive elements of the detector 15 as a function of the mean X-ray photon flux received by the whole set or some of the photosensitive elements of the detector 15.

In the case of successive acquisitions over time, the X-ray photon flux considered for the determination of the cutoff frequency for a given acquisition, of order A, may be the photon flux determined during the previous acquisition, of order A−1. For luggage checking applications where the luggage moves at constant speed, each acquisition corresponds to a length of the order of a millimeter. This length being relatively small with respect to the length of the objects to be analyzed, the variation of the photon flux is relatively small and leads to a good approximation of the photon flux for the current acquisition.

The X-ray photon flux received by each photosensitive element of the detector 15 can be determined according to two embodiments. According to a first embodiment, the total photonic energy $E_T$ received is determined in a first step. This energy corresponds to the integral of the signal delivered by the photosensitive element considered during the previous acquisition. It can be determined through the following equation:

$$E_T = \sum_{t=0}^{P-1} s_t$$

with $s_t$ the t-th signal sample, and P the number of samples in the acquisition. In a second step, the mean photonic energy $E_M$ of the X-ray photons received is determined. This energy can be determined through the following equation:

$$E_M = \frac{\sum_{i=0}^{C-1} E_i N_i}{\sum_{i=0}^{C-1} N_i}$$

with $E_i$ the i-th energy class, $N_i$ the number of photons (occurrences) in this energy class, and C the number of energy classes.

In a third step, the ratio of the total photonic energy $E_T$ to the mean photonic energy $E_M$ is determined. This ratio $N_{eff}$ corresponds to the effective number of X-ray photons received during the previous acquisition. Knowing the duration of this acquisition, the X-ray photon flux can be deduced therefrom. This first embodiment exhibits the advantage of not requiring calibration.

According to a second embodiment, the total photonic energy $E_T$ received is determined in a first step, as indicated previously. In a second step, the X-ray photon flux received is determined on the basis of this integral and of a predetermined table of values. The table of values is established beforehand during a calibration. The calibration consists in determining, for various levels of photon flux, the integral of the signal associated with each level of photon flux. This second embodiment exhibits the advantage of requiring little real-time calculation.

The adjusting of the cutoff frequency of the low-pass filter of the shaping circuit 162 allows tailoring to the X-ray photon flux received at a first level. The processing device 16 according to the invention can furthermore be tailored to the X-ray photon flux at a second level, namely at the level of the generation of the energy spectrum. For this purpose, the energy spectrum is smoothed by the smoothing filter 165 comprising a low-pass filter whose cutoff frequency is adjusted as a function of the X-ray photon flux. The bigger the X-ray photon flux, the lower the cutoff frequency. The low-pass filter can for example be achieved by adjusting the number of classes of the energy spectrum. The bigger the X-ray photon flux, the more reduced the number of classes, the energy ranges then being widened.

Figure 3:
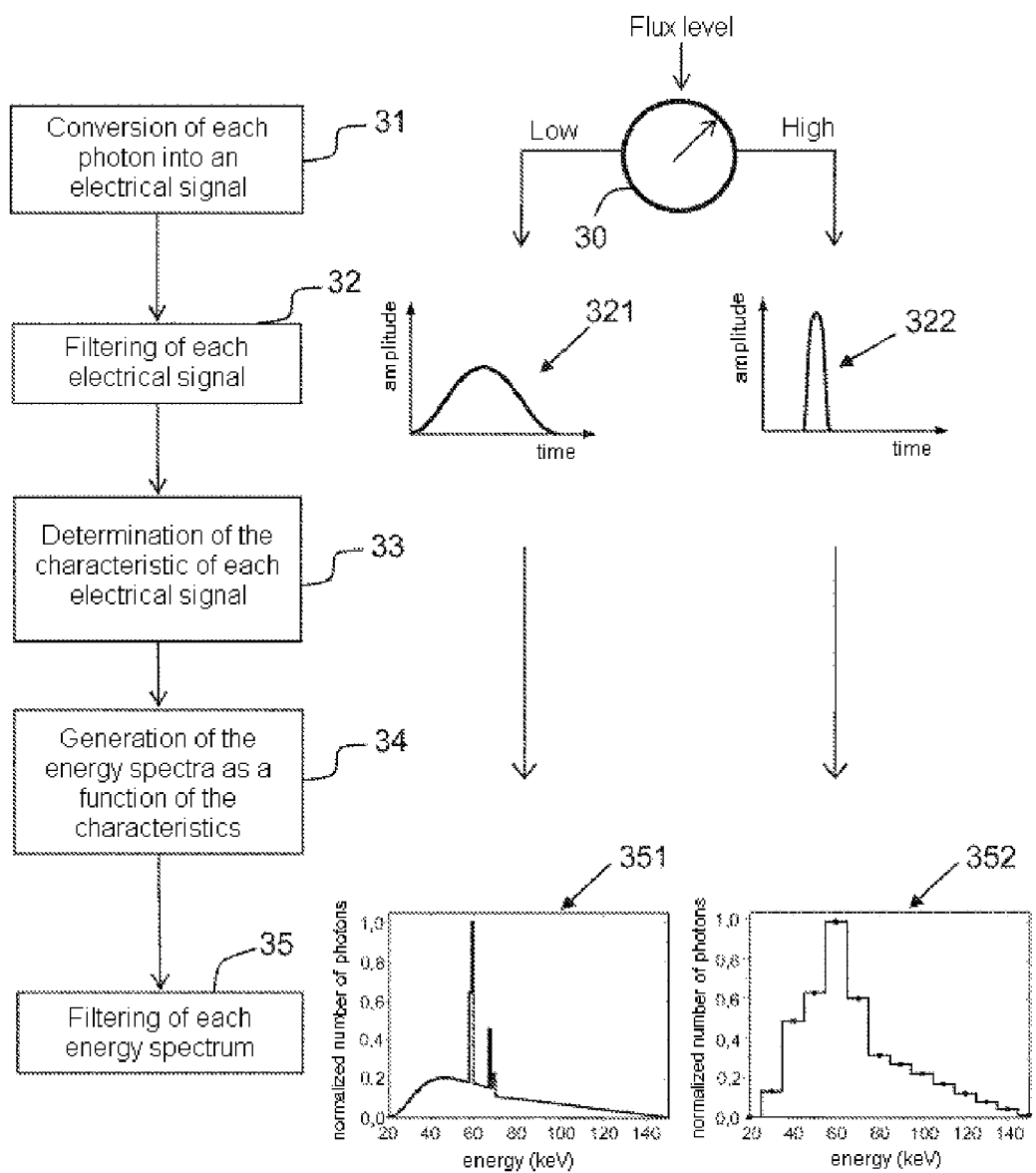
FIG. 3 represents, in the form of a chart, an exemplary processing method according to the invention.

FIG. 3 represents, in the form of a chart, an exemplary processing method according to the invention. In this method, the cutoff frequencies of the filterings carried out for the construction of the energy spectrum are adjusted as a function of the level of the photon flux. The level of the photon flux is for example determined during the previous acquisition. In FIG. 3, it is represented symbolically by a gauge 30 that can take various values between a minimum flux level and a maximum flux level. In a first step 31, each photon received by a photosensitive element is converted into an electrical signal, a characteristic of which is representative of its energy. The electrical signal is for example a voltage pulse. In a second step 32, each voltage pulse or, more generally, each electrical signal, a characteristic of which is representative of the energy of the photon received, is filtered by the low-pass filter of the shaping circuit 162. The bigger the level of the X-ray photon flux, the higher the cutoff frequency of this low-pass filter. In FIG. 3, the impact of the filter is represented in the form of two graphs 321 and 322. The first graph 321 corresponds to a small flux level, and therefore to a low cutoff frequency. The second graph 322 corresponds to a large flux level, and therefore to a high cutoff frequency. In the temporal domain, a low cutoff frequency gives a signal whose shape is spread over time, and a high cutoff frequency gives a larger-amplitude signal that is less spread over time. In a third step 33, the integral of each pulse or, more generally, the characteristic of each electrical signal is determined. In a fourth step 34, an energy spectrum is constructed for each acquisition and for each photosensitive element. Each spectrum is constructed as a function of the characteristic of the various electrical signals of the acquisition. In a fifth step 35, the energy spectra are filtered by a low-pass filter. The bigger the photon flux, the lower the cutoff frequency of this filter. In FIG. 3, two energy spectra 351 and 352 are represented. The first spectrum 351 represents an exemplary filtered spectrum obtained for a small flux level. The second spectrum 352 represents an exemplary filtered spectrum obtained for a large flux level. The resolution of the spectrum 351 is markedly inferior to that of the spectrum 352.

Various signal processing operations can be carried out on completion of the construction of the energy spectra. These entail for example correction of pileups, that is to say the deletion, by processing, of two successive photons converted into a single electrical signal, whose characteristics make it possible to identify it as such. These may also involve correction of the splitting of the charges, that is to say the reconstruction of a single pulse on the basis of two pulses arising from a single photon received by two adjacent photosensitive elements. In so far as the voltage pulses of the large fluxes are filtered with a high cutoff frequency, that is to say with a short time constant, a correction of pileups and a correction of the splitting of the charges can almost always be carried out.

The invention claimed is:

1. A processing method for a spectrometric measurement in terms of energy of a photon flux received by a photosensitive element of a detector, the method comprising the following successive steps:
converting each photon received by the photosensitive element into packets of electrical charges and converting said packets of electrical charges in an electrical signal with a preamplifier, a characteristic of which is representative of the energy of the photon considered,
filtering each electrical signal with a first low-pass filter of a shaping circuit whose cutoff frequency is adjusted as a function of the photon flux received by the photosensitive element, such that the greater the flux, the higher the cutoff frequency,
determining a characteristic of each filtered electrical signal with a measurement circuit,
generating an energy spectrum for the photon flux received with a spectrum generator as a function of the characteristic of the filtered electrical signals, and
filtering an energy spectrum with a second low-pass filter being a low-pass filter of a smoothing filter whose cutoff frequency is adjusted as a function of the photon flux provided by the spectrum generator, such that the greater the flux, the lower the cutoff frequency.

2. The method as claimed in claim 1, wherein the energy spectrum is generated in a form of a histogram in which classes are distinct energy ranges, an occurrence of each class being a number of photons whose energy lies in the energy range of the class considered, the cutoff frequency of the second low-pass filter being determined by a number of classes of the histogram, the greater the flux, the fewer classes the histogram comprises.

3. The method as claimed in claim 1, wherein each photon received by the photosensitive element is converted into a pulse whose integral is proportional to the energy of the photon considered.

4. The method as claimed in claim 1, wherein the photon flux is received during a predetermined acquisition interval, the cutoff frequencies of the first and of the second low-pass filter being adjusted as a function of the photon flux determined from a previous acquisition interval.

5. The method as claimed in claim 4, wherein the photon flux is determined by the following steps:
determining a total photonic energy $E_T$ received by the photosensitive element during the previous acquisition interval,
determining a mean photonic energy $E_M$ of the photons received by the photosensitive element during the previous acquisition interval,
determining a ratio $N_{eff}$ of the total photonic energy $E_T$ to the mean photonic energy $E_M$, a quotient of said ratio $N_{eff}$ over a duration of the previous acquisition interval giving the photon flux.

6. A processing device for a spectrometric measurement in terms of energy of a photon flux that may be received by a photosensitive element of a detector, the photosensitive element converting each photon into packets of electrical charges, the device comprising:
a preamplifier configured to convert said packets of electrical charges into an electrical signal, a characteristic of which being representative of the energy of the photon,
a shaping circuit comprising a first low-pass filter filtering each electrical signal, the cutoff frequency of the first low-pass filter being adjusted as a function of the photon flux received by the photosensitive element, such that the greater the flux, the higher the cutoff frequency,
a measurement circuit determining a characteristic of each filtered electrical signal,
a spectrum generator configured to generate an energy spectrum for the photon flux received as a function of the characteristic of the filtered electrical signals, and
a smoothing filter comprising a second low-pass filter filtering the energy spectrum, the cutoff frequency of the second low-pass filter being adjusted as a function of the photon flux generated by the spectrum generator, such that the greater the flux, the lower the cutoff frequency.

7. The method as claimed in claim 1, wherein the energy spectrum is generated in a form of a histogram in which classes are distinct energy ranges, an occurrence of each class being a number of photons whose energy lies in the energy range of the class considered, the cutoff frequency of the second low-pass filter being adjusted such that, a number of classes contained in the histogram of a smoothed energy spectrum obtained by filtering the energy spectrum by the smoothing filter such that the greater the flux, the fewer the number of classes contained in the histogram of the smoothed energy spectrum such that the energy ranges are widened.

8. A processing method for a spectrometric measurement in terms of energy of a photon flux received by a photosensitive element of a detector, the method comprising the following successive steps:
converting each photon received by the photosensitive element into packets of electrical charges and converting said packets of electrical charges into an electrical signal with a preamplifier, a characteristic of which is representative of the energy of the photon considered,
filtering each electrical signal with a first low-pass filter of a shaping circuit in response to an output from the preamplifier,
determining a characteristic of each filtered electrical signal with a measurement circuit,
generating an energy spectrum for the photon flux received with a spectrum generator as a function of the characteristic of the filtered electrical signals, and
filtering an energy spectrum with a second low-pass filter being a low pass filter of a smoothing filter in response to an output from the spectrum generator.

9. The method as claimed in claim 8, wherein the energy spectrum is generated in a form of a histogram in which classes are distinct energy ranges, an occurrence of each class being a number of photons whose energy lies in an energy range of the class considered.

10. The method as claimed in claim 8, wherein each photon received by the photosensitive element is converted into a pulse whose integral is proportional to the energy of the photon considered.

11. The method as claimed in claim 8, wherein the photon flux is received during a predetermined acquisition interval, the first and of the second low-pass filter being responsive to the photon flux determined from a previous acquisition interval.

12. The method as claimed in claim 11, wherein the photon flux is determined by the following steps:
determining a total photonic energy $E_T$ received by the photosensitive element during the previous acquisition interval,
determining a mean photonic energy $E_M$ of the photons received by the photosensitive element during the previous acquisition interval,
determining a ratio $N_{eff}$ of the total photonic energy $E_T$ to the mean photonic energy $E_M$, a quotient of said ratio $N_{eff}$ over a duration of the previous acquisition interval giving the photon flux.

13. The method as claimed in claim 8, wherein the energy spectrum is generated in a form of a histogram in which classes are distinct energy ranges, an occurrence of each class being a number of photons whose energy lies in the energy range of the class considered, the second low-pass filter operating in response to the energy spectrum such that, a number of classes contained in the histogram of a smoothed energy spectrum obtained by filtering the energy spectrum by the smoothing filter such that the greater the flux, the fewer the number of classes contained in the histogram of the smoothed energy spectrum such that the energy ranges of the classes are widened.

* * * * *